(12) United States Patent
Deppermann et al.

(10) Patent No.: US 7,401,528 B2
(45) Date of Patent: Jul. 22, 2008

(54) APPARATUS AND METHODS FOR EVALUATING PLANT STALK STRENGTH

(75) Inventors: Kevin L. Deppermann, St. Charles, MO (US); Mike Bohnert, Ames, IA (US); Jason Bull, St. Louis, MO (US); Jeremy Conry, Ankeny, IA (US); Kevin Cook, Ankeny, IA (US); Sam Eathington, Ames, IA (US); Travis Frey, Huxley, IA (US); Jeff Hartsook, Madrid, IA (US); Bruce Schnicker, Wildwood, MO (US); Jeremy Nefzger, Dyersville, IA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/766,485

(22) Filed: Jun. 21, 2007

(65) Prior Publication Data
US 2007/0294994 A1 Dec. 27, 2007

Related U.S. Application Data

(60) Provisional application No. 60/815,775, filed on Jun. 22, 2006.

(51) Int. Cl.
*G01N 3/08* (2006.01)
*G01N 3/20* (2006.01)
*A01D 41/127* (2006.01)
*A01D 45/00* (2006.01)

(52) U.S. Cl. .................. 73/826; 73/865.3; 56/10.2 R; 56/12.4; 56/12.9

(58) Field of Classification Search ............ 73/862.393, 73/828, 829, 865.3, 783, 781, 788, 789, 805, 73/826; 47/1.7; 56/10.2 R, 10.3, 11.6, 12.4, 56/12.5, 12.9, 56
See application file for complete search history.

(56) References Cited

U.S. PATENT DOCUMENTS 3,548,570 A * 12/1970 Suggs et al. ............. 56/10.2 R
5,044,210 A * 9/1991 Kuhn et al. ................ 73/865.3
6,983,582 B1 * 1/2006 Muckler ......................... 56/1

FOREIGN PATENT DOCUMENTS

WO WO 2007/061534 5/2007

* cited by examiner

*Primary Examiner*—Edward Lefkowitz
*Assistant Examiner*—Punam Patel
(74) *Attorney, Agent, or Firm*—James E. Davis; Joseph A. Schaper; Harness, Dickey & Pierce, P.L.C.

(57) ABSTRACT

An apparatus for measuring stalk strength and/or root strength of a plant is provided. In accordance with various embodiments, the apparatus includes a conveyer operably connected to a motor for circulatorily driving the conveyer around at least one guide device. At least one pulling finger is coupled to the conveyer. Each pulling finger is structured such that, when the apparatus is positioned adjacent the plant stalk and the conveyor is driven around the guide device, each pulling finger will contact and pull a plant stalk as each pulling finger travels around the guide device. The apparatus additionally includes a force sensor for measuring resistive force encountered by the motor as each pulling finger pulls the plant stalk.

27 Claims, 8 Drawing Sheets

APPARATUS AND METHODS FOR EVALUATING PLANT STALK STRENGTH

CROSS-REFERENCE TO RELATED APPLICATIONS

This application claims the benefit of U.S. Provisional Application No. 60/815,775, filed on Jun. 22, 2006. The disclosure of the above application is incorporated herein by reference in its entirety.

FIELD

The present disclosure relates to the testing and development of new plant hybrids in a plant breeding program, and particularly to apparatuses and methods for evaluating the strength of a plant stalk.

BACKGROUND

The statements in this section merely provide background information related to the present disclosure and may not constitute prior art.

Green snap is a weather-induced breaking of the corn stalk below the primary ear node (Wilhelm, et al., 1999). Snapping typically occurs during the five to eight leaf and/or the twelve leaf to tasseling stages of corn growth. These periods of increased susceptibility are due to the rapid rate of internode elongation. Generally, green snap is localized to a small area or a particular hybrid within a field. However, green snap has the potential to cause millions of dollars in damage to crops over wide areas. For example, on Jul. 8, 1993 a devastating storm caused an estimated $200 million of damage to Nebraska crops (Benson, 2001; Wilhelm et. al., 1999).

Strategies for protecting against green snap have included late planting, exclusion of growth regulator herbicides, suboptimal nitrogen rates, and monoculture (Wilhelm, et. al., 1999). While these strategies have demonstrated potential to protect against green snap, each strategy has resulted in limiting overall yield. Therefore, these methods are not effective or economical for large-scale protection against green snap damage.

Many industry professionals have suggested that in-seed protection is the best way to offer resistance to green snap. In general, strong, deep-rooted hybrids will suffer more than flexible, shallowly rooted hybrids from fast, damaging winds. Levels of lignin production and timing also play a role in green snap resistance. During rapid growth stages, lignin production cannot keep up with the rapidly elongating corn stalk, which compromises the stability and strength of the plant. In-seed breading of these traits can provide protection against green snapping.

Similarly, stalk lodging is the weather-induced breaking of the stalk below the ear. Stalk lodging results in increased harvest losses, slower harvest equipment speeds, increased drying cost and, in most cases, a significant volunteer problem next season. Yield losses from stalk lodging can range from five to twenty-five percent nationwide. Three main causes of stalk lodging are late season severe weather, damage to the stalk by the European corn borer and the stalk rot disease complex. The incidence and severity of stalk rot in any field will depend on the genetic susceptibility of the hybrid, the presence and virulence of the stalk rot organisms and the environmental conditions during the growing season. Almost all stress factors during the growing season can predispose the corn plant to invasion by stalk rot fungi. Management systems to reduce stress in the field include proper hybrid selection, proper plant population, adequate moisture at critical times, full fertility programs, insect control, crop rotation and timely scouting.

SUMMARY

In various embodiments, the present disclosure provides an apparatus for measuring stalk strength and/or root strength of a plant that includes a conveyer operably connected to a motor for circulatorily driving the conveyer around at least one guide device. At least one pulling finger is coupled to the conveyer. Each pulling finger is structured such that, when the apparatus is positioned adjacent the plant stalk and the conveyor is driven around the guide device, each pulling finger will contact and pull a plant stalk as each pulling finger travels around the guide device. The apparatus additionally includes a force sensor for measuring resistive force encountered by the motor as each pulling finger pulls the plant stalk.

In various other embodiments, the present disclosure provides a system for measuring stalk strength and/or root strength of a crop plant that includes a plant stalk strength measuring (PSSM) apparatus. In various implementations, the PSSM apparatus includes a conveyer operably connected to a motor for circulatorily driving the conveyer around at least one guide device. A plurality of pulling fingers are coupled to the conveyer. Each pulling finger is structured such that, when the PSSM apparatus is sequentially positioned adjacent each plant stalk in the crop and the conveyor is driven around the guide device, the pulling fingers will sequentially contact and pull a respective plant stalk as each pulling finger travels around the guide device.

The PSSM apparatus further includes a force sensor for measuring resistive force encountered by the motor as the pulling fingers pull the plant stalks. The system additionally includes a positioning mechanism mountable to a vehicle, e.g., a tractor. The positioning mechanism is structured to suspend and position the PSSM apparatus such that the PSSM apparatus will sequentially contact, and the pulling fingers will sequentially pull each plant stalk in a subject row of the plants, as the vehicle moves along the subject row of plants.

In still other embodiments, the present disclosure provides a method for automatically measuring stalk strength and/or root strength of a plurality of plants. The method includes moving a plant stalk strength measuring (PSSM) apparatus along a subject row of plants. The PSSM apparatus sequentially contacts and laterally pulls each stalk in a subject row utilizing a plurality of pulling fingers that are circulatorily traveling around at least one PSSM apparatus guide device. The method further includes measuring and compiling resistive forces encountered by a motor driving the pulling fingers around the guide device as each pulling finger pulls a respective one of the plant stalks.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

It should be understood that throughout the drawings, corresponding reference numerals indicate like or corresponding parts and features.

DETAILED DESCRIPTION

Figure 1:
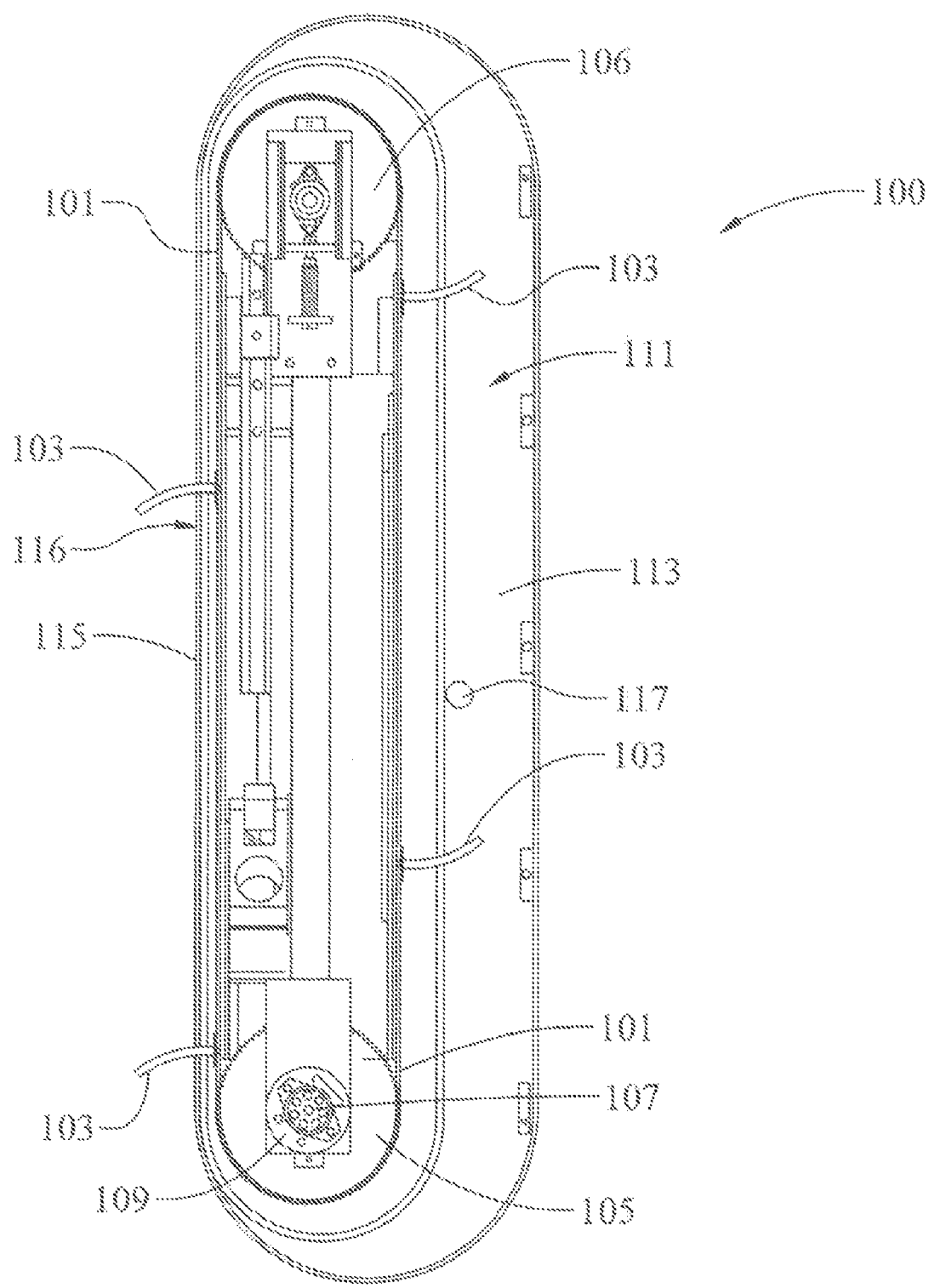
FIG. 1 is a top view of an apparatus for measuring plant stalk strength having a top half the housing removed, in accordance with various embodiments of the present disclosure.

The following description is merely exemplary in nature and is in no way intended to limit the present teachings, application, or uses. Throughout this specification, like reference numerals will be used to refer to like elements.

The present disclosure provides systems, apparatuses and methods for automatically accurately measuring plant stalk strength of independent plant stalks within a field of stalks. The data collected can then be used to measure, analyze and predict resistance of various hybrids to green snap, stalk lodging and/or root lodging. For example, the present systems, apparatuses and methods can be utilized by breeders to distinguish small differences in snapping and/or lodging resistance. The data can then be used to segregate populations and facilitate the mapping of QTL.

As used herein, the term "inbred" means a line that has been bred for genetic homogeneity. Without limitation, examples of breeding methods to derive inbreds include pedigree breeding, recurrent selection, single-seed descent, backcrossing, and doubled haploids.

As used herein, the term "hybrid" means a progeny of mating between at least two genetically dissimilar parents. Without limitation, examples of mating schemes include single crosses, modified single cross, double modified single cross, three-way cross, modified three-way cross, and double cross, wherein at least one parent in a modified cross is the progeny of a cross between sister lines.

As used herein, "genetic marker" means polymorphic nucleic acid sequence or nucleic acid feature. A "polymorphism" is a variation among individuals in sequence, particularly in a DNA sequence, or feature, such as a transcriptional profile or methylation pattern. Useful polymorphisms include single nucleotide polymorphisms (SNPs), insertions or deletions in DNA sequence (Indels), simple sequence repeats of DNA sequence (SSRS) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In other embodiments, the genotype can reflect the sequence of a portion of a chromosome, an entire chromosome, a portion of the genome, and the entire genome.

As used herein, "phenotype" means the detectable characteristics of a cell or organism which are a manifestation of gene expression.

As used herein, "quantitative trait locus (QTL)" means a locus that controls to some degree numerically representable traits that are usually continuously distributed.

Referring to FIG. 1, a plant stalk strength measurement (PSSM) apparatus 100 is provided, in accordance with various embodiments. Generally, the PSSM apparatus 100 includes a closed-loop conveyer 101 having at least one curved, or hooked, stalk pulling finger 103 mounted thereto. The closed-loop conveyer 101 is connected around a drive device 105 and at least one slack limiting guide device 106. The drive device 105 is driven by a pulling motor 107 that is operable to circulatorily drive the conveyer 101 around the drive device 105 and the slack limiting guide device(s) 106. More particularly, the pulling motor 107 circulatorily drives the stalk pulling finger(s) 103, mounted to the conveyer 101, around the drive device 105 and slack limiting guide device(s) 106.

The closed-loop conveyer 101 can be any elongated, flexible component suitable to be circulatorily driven by the pulling motor 107 and drive device 105 around the drive device 105 and the slack-limiting guide device(s) 106. For example, in various embodiments, the conveyer 101 can be a chain, belt, cable, etc. The pulling motor 107 can be any motor suitable for imparting a force on the drive device 105 to cause the drive device 105 to move and thereby circulatorily drive the conveyer 101 and finger(s) 103 around the drive device 105 and the slack-limiting guide device(s) 106. For example, in various embodiments, the pulling motor 107 can be an electrically, pneumatically or hydraulically operated rotary or linear motor. Accordingly, the drive device 105 can be any device suitable to be driven, or moved, by the force imparted by the pulling motor 107 and in turn circulatorily drive the conveyer 101 and finger(s) 103 around the drive device 105 and the slack-limiting guide device(s) 106. For example, in various embodiments the drive device 105 can be a sprocket, or pulley wheel driven by a rotary motor 107. Or, in various other embodiments, the drive device 105 can be a threaded shaft driven by a linear motor 107. Similarly, the slack-limiting guide device(s) 106 can be a sprocket or pulley.

Additionally, although the (PSSM) apparatus 100 can include one or more stalk pulling fingers 103 and one or more slack-limiting guide devices 106, for clarity and simplicity, the PSSM apparatus 100 will be described herein as including a plurality of stalk pulling fingers 103 and a single slack-limiting guide device 106.

Generally, the PSSM apparatus 100 is moved along a row of plants, e.g., corn, wheat, canola, sunflower, and sorghum, while the pulling motor 107 and drive device 105 are driving the conveyer and pulling fingers 103 around the drive device 105 and the slack-limiting guide device 106. The PSSM apparatus 100 is positioned such that as the PSSM apparatus 100 is moved along the row of plants one of the circulatorily moving pulling fingers 103 contacts and 'hooks' a corresponding individual plant stalk. Subsequently, as the respective pulling finger 103 continues to move around the drive device 105 and slack-limiting guide device 106, the 'hooked' stalk will be pulled in a lateral and downward direction. The pulling finger 103 will continue to pull the stalk laterally and downward until the stalk snaps, breaks, bends or dislodges.

The PSSM apparatus 100 additionally includes a force sensor 109 operable to measure the amount of force, e.g., torque, generated by the pulling motor 107 to advance the conveyer 101 and pulling fingers 103 to break the respective stalk. That is, the force sensor 109 measures the resistive force, e.g., torque, exerted by the stalk against the movement of the pulling motor 107, via the pulling finger 103, conveyer 101 and drive device 105, as the stalk is pulled and broken, bent or dislodged. As the PSSM apparatus continues to be moved along the row of plants, a subsequent pulling finger 103 contacts and pulls a subsequent plant stalk. The force sensor 109 then measures the force required, e.g., torque, to break, bend or dislodge the respective plant stalk. The force data, e.g., torque data, is collected and analyzed to predict the resistance of various hybrids to green snap, stalk lodging and/or root lodging.

Figure 2:
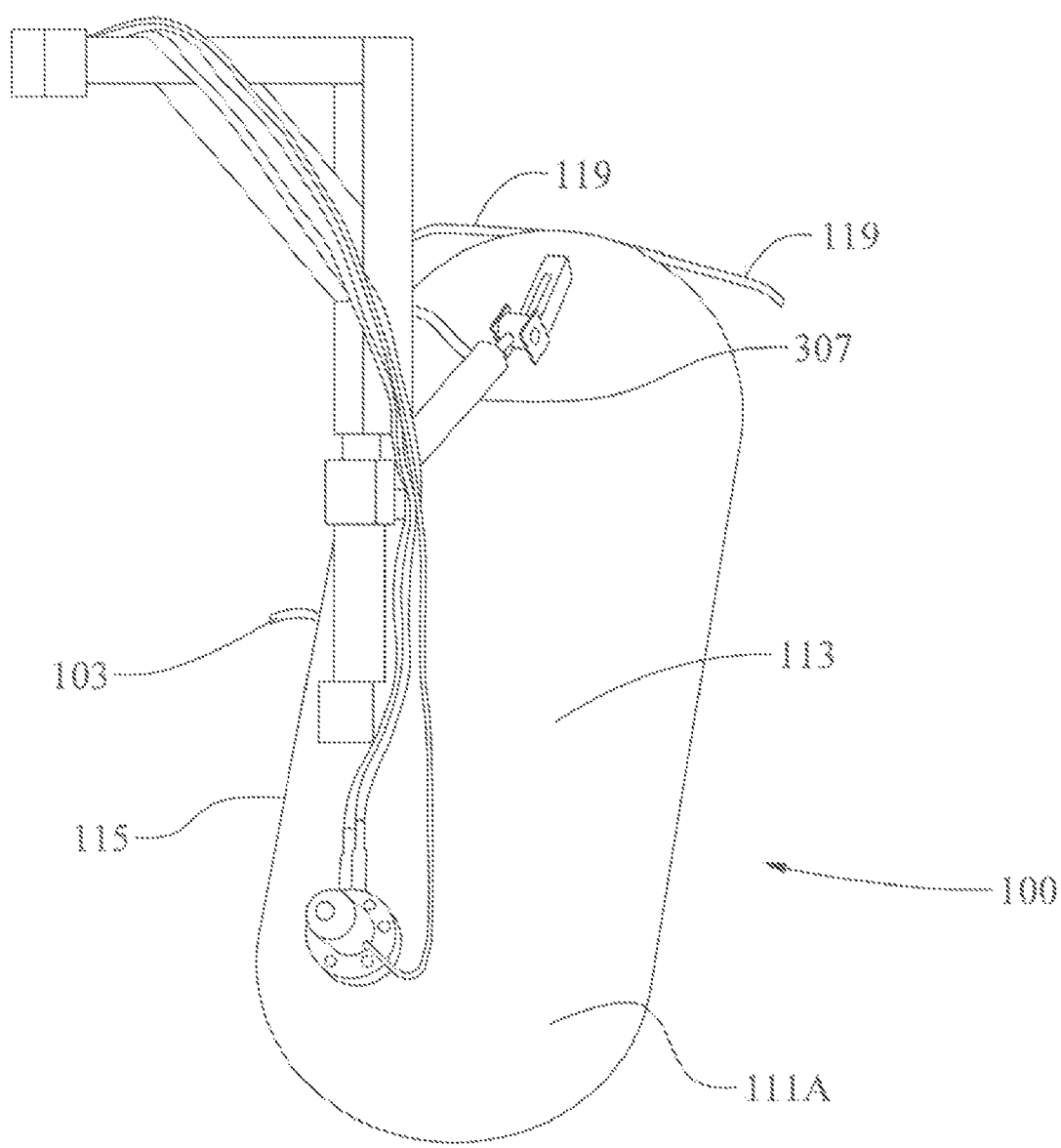
FIG. 2 is a top view of the apparatus for measuring plant stalk strength shown in FIG. 1 including the top half of the housing, in accordance with various embodiments of the present disclosure.

Referring now to FIGS. 1 and 2, the stalk pulling components described above, i.e., the conveyer 101, pulling fingers 103, drive device 105, slack-limiting guide device 106, pulling motor 107, force sensor 109, etc., are enclosed within a housing 111. A top half 111A (shown in FIG. 2) of the housing 111 is removed in FIG. 1 to illustrate the stalk pulling components. The housing 111 protects the conveyor 101, drive device 105, slack-limiting guide device 106, pulling motor 107 and force sensor 109 from damage and interference by non-subject stalks, i.e., stalks that are not presently engaged and being pulled, and inadvertent human contact. The housing 111 is further structured to enclose non-engaged pulling fingers 103, i.e., pulling fingers 103 not presently engaged with and pulling a respective subject stalk, within a non-contact portion 113 of the housing 111. More specifically, in such embodiments, the housing 111 is structured to cover and protect the pulling fingers 103 as the pulling fingers 103 travel within the non-contact portion 113 of the housing 111, i.e., a trailing portion of the housing 111 that will not contact the subject stalks as they are being pulled.

Thus, as the pulling fingers 103 travel along the circulatory path of the conveyer 101, each pulling finger will be unexposed, i.e., enclosed within the housing 111, until each pulling finger 103 reaches an engagement portion of the circulatory path, i.e., a leading edge 115 of the housing 111. At which point, at least a large section of each respective pulling finger 103 will emerge through a pulling finger travel slot 116 (best shown in FIG. 7) in the edge of the housing 111 and extend outwardly outside the leading edge 115 of the housing 111. The respective exposed pulling finger 103 with then engage, i.e., hook, a respective plant stalk, and pull the plant stalk laterally and downward (due to a snap angle of the PSSM 100, as described below) along the leading edge 115 until the plant stalk breaks, bends or dislodges. The respective pulling finger 103 will then continue along the circulatory path within travel slot and then retract back within the non-contact portion 113 of the housing 111.

In various embodiments the PSSM apparatus 100 further includes a finger sensor 117 operable to sense the position of each respective finger along the circulatory travel path of the conveyer 101 and pulling fingers 103. Additionally, the finger sensor 117 provides finger count data that is used to correlate the force data, e.g., torque data, collected by the force sensor 109 with the respective stalks that each pulling finger 103 engages. That is, the finger sensor 117 can be used to count the number of pulling fingers cycled past the finger sensor 117 and that number can be cross-referenced with the force data collected to parse out any skewed data, i.e., data resulting from double or missed pulls. Furthermore, the finger sensor 117 can be utilized to start and stop data acquisition between plants.

Figure 3:
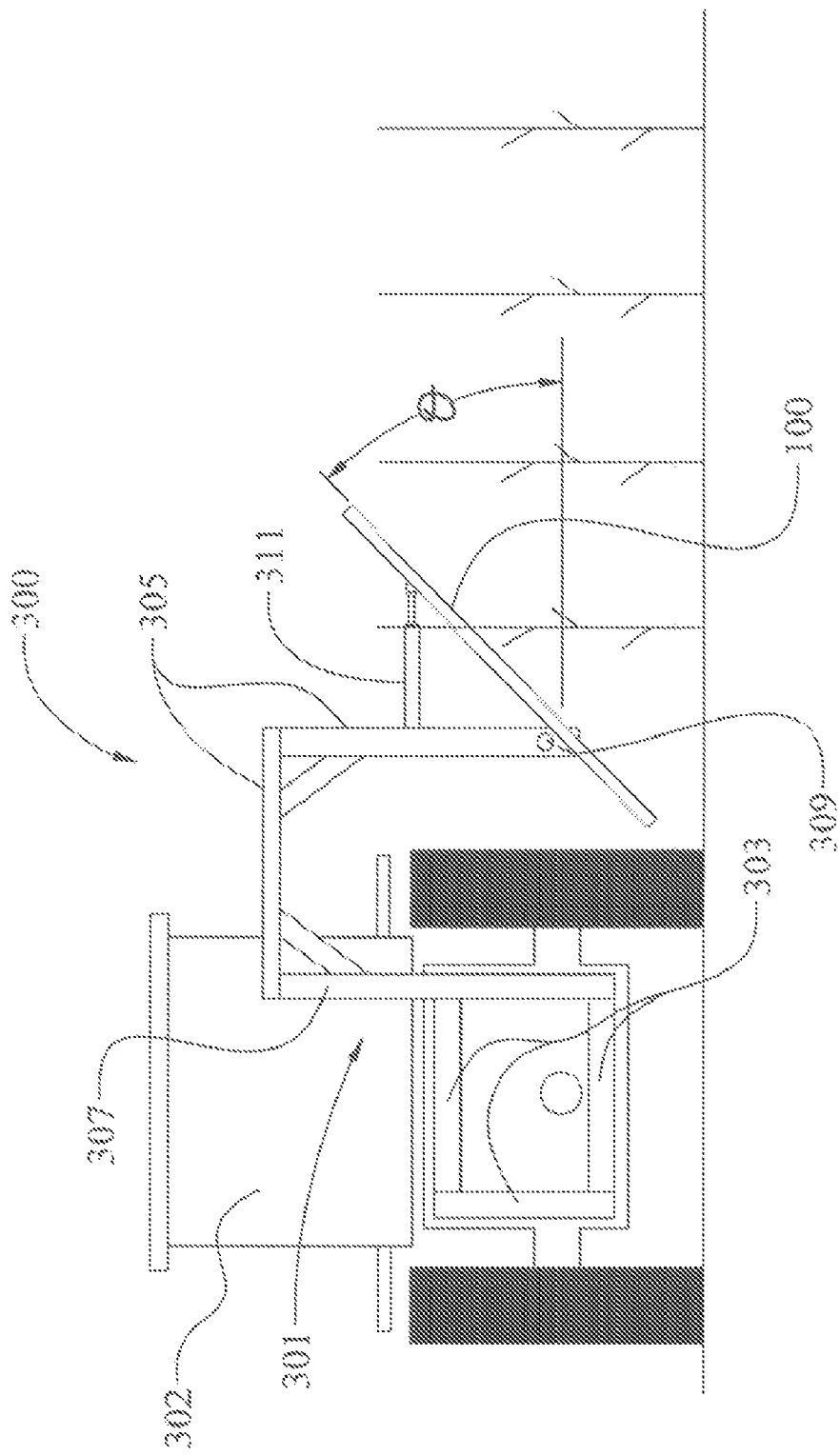
FIG. 3 is a schematic of a rear elevation view of a system for measuring plant stalk strength, including the apparatus for measuring plant stalk strength shown in FIG. 1, in accordance with various embodiments of the present disclosure.

Referring now to FIG. 3, in various embodiments, the PSSM apparatus 100 is part of a vehicle mountable system 300 for measuring plant stalk strength. In various forms, the system 300 includes a positioning mechanism 301 that is mounted to a tractor 302 or other suitable vehicle for moving the PSSM apparatus 100 along a plot of crop plants. The positioning mechanism 301 is structured to suspend and position the PSSM apparatus 100 such that the PSSM apparatus 100 will contact and bend, break or dislodge each plant stalk in a row as the tractor 302 moves along the row of plants. The positioning mechanism 301 includes a mounting structure 303 and a jib arm 305 pivotally connected to the mounting structure 303. The mounting structure 303 is configured to mount to the tractor 302, via any suitable mounting means, e.g., a standard Class 2 three-point hitch. The mounting structure 303 includes a telescoping post 307 that has the jib arm 305 pivotally coupled to a top portion of the telescoping post 307. The PSSM apparatus 100 is pivotally mounted to a distal end of the jib arm 305 such that the jib arm 305 suspends and positions the PSSM apparatus 100 adjacent the tractor 302. The telescoping post 307 is operable to adjust the height of the jib arm 305 and PSSM apparatus 100, i.e., raise and lower the jib arm 305 to position the PSSM apparatus 100 at a desired distance above the ground. Additionally, the jib arm 305 is pivotally coupled to the telescoping post 307 such that PSSM apparatus 100 can be swiveled, or pivoted, around the telescoping post 307. Accordingly, the height and angular position, relative to the telescoping post 307, of the PSSM apparatus 100 can be adjusted as desired.

In various embodiments, the telescoping function of the telescoping post 307 and the pivotal positioning of the jib arm 305 about the telescoping post 307 are automated. However, in various embodiments, the telescoping function of the telescoping post 307 and the pivotal positioning of the jib arm 305 about the telescoping post 307 can be manually adjustable.

Additionally, the PSSM apparatus 100 is pivotally attached to the distal end of the jib arm 305 via a pivot joint 309 and a telescoping adjustment arm 311. The telescoping adjustment arm 311 can be any suitable apparatus that can extend and retract to adjust a snap angle $\theta$ of the PSSM apparatus 100, e.g., a hydraulic or pneumatic piston or a threaded turnbuckle. The snap angle θ is the angle of PSSM apparatus 100 relative to a plane substantially parallel to the ground and defines the angle at which force is applied to the plant stalks as the pulling fingers 103 hook and pull each respective plant stalk. The snap angle θ can be incorporated and analyzed along with the force data collected to predict the resistance of various hybrids to green snap, stalk lodging and/or root lodging. In various embodiments, the snap angle θ can be set to any angle between −10° to +65°, inclusive. For example, in various embodiments, the snap angle θ is set to approximately 20°, such that as a pulling finger 103 hooks a respective stalk, the stalk is pulled laterally and downward at a 20° angle.

Figure 4:
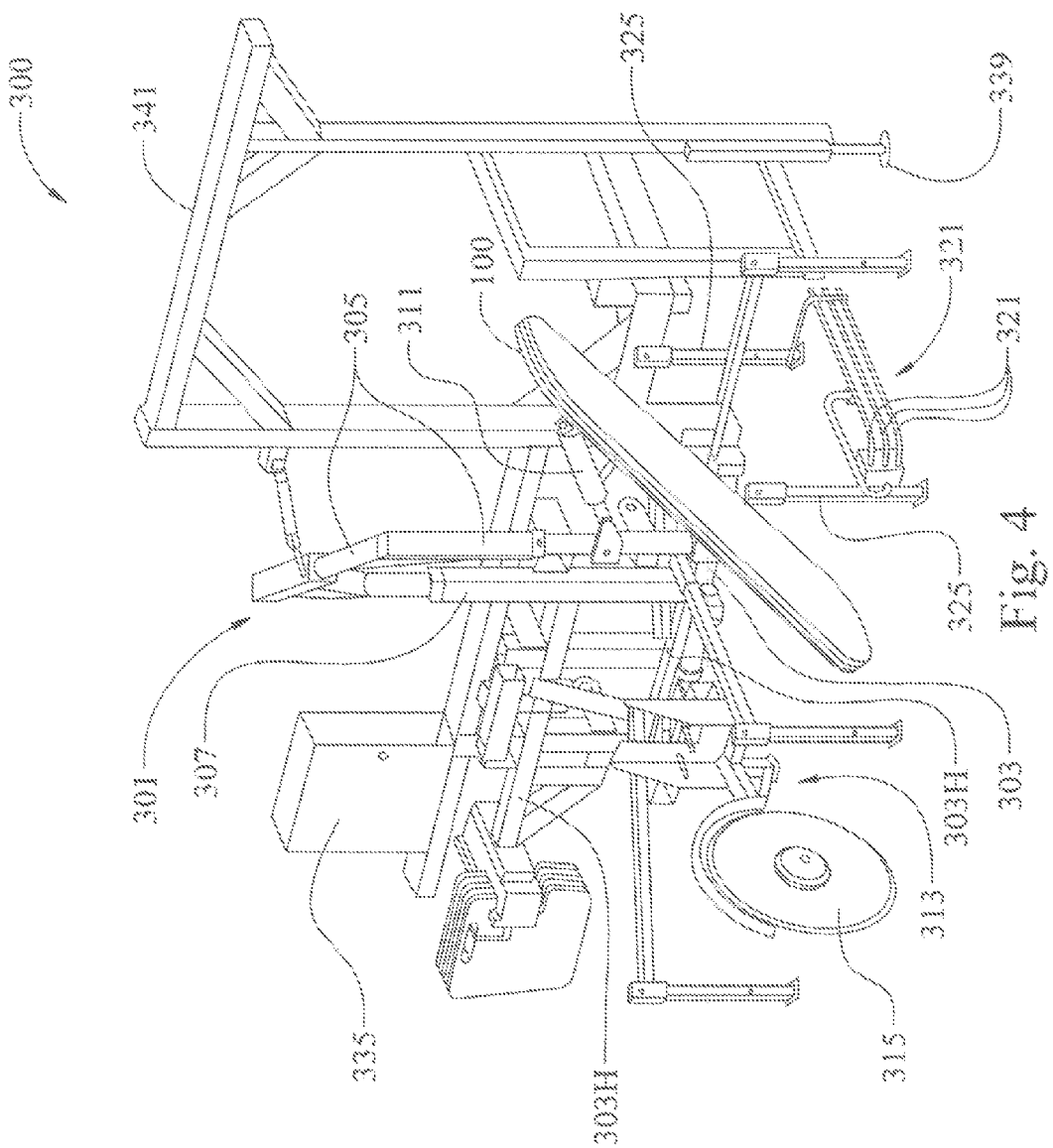
FIG. 4 is an isometric view of the system for measuring plant stalk strength, shown in FIG. 3, in accordance with various other embodiments of the present disclosure.

Referring now to FIG. 4, in various other forms, the system 300 further includes a guide assembly 313 attached to the mounting structure 303 for assisting the lateral positioning of the PSSM apparatus 100 as the tractor 310 (shown in FIG. 3) moves along the plot of crop plants. In various embodiments, the guide assembly 313 includes a cultivar guidance wheel 315 that provides lateral stability to the positioning mechanism 301, thereby aiding the lateral positioning of the PSSM apparatus 100 as the tractor 310 moves along the plot of crop plants. In various embodiments, the system 300 additionally includes an anti-lodge assembly 321 removably attached to the mounting structure 303 via support legs 325. The anti-lodge assembly 321 is implemented when the system 300 and PSSM apparatus 100 are utilized to collect green snap and stalk lodging data. The anti-lodge assembly is removed when the system 300 and PSSM apparatus 100 are utilized to collect root lodging data during green snap and stalk lodging testing, the anti-lodge assembly 321 is positioned such that as the PSSM apparatus 100 is moved along the row of plants, the anti-lodge assembly 321 provides support for the base of each stalk as the PSSM apparatus 100 pulls the stalks laterally and downward. Thus, the anti-lodge assembly 321 prevents root lodging when collecting stalk strength data, i.e., green snap and stalk lodging data. The anti-lodge assembly 321 can be positioned at different heights on the support legs 325 to thereby more consistently set the stalk snapping height to a desired position. For example, the anti-lodge assembly 321 can be positioned at different heights on the support legs 325 depending on the type of germ pods under test. Additionally, in various embodiments, the anti-lodge assembly 321 includes one or more adjustable bars 329 that can be changed or reconfigured to provide adjustable contour shapes for bending the stalk to contact while being snapped.

Figure 5:
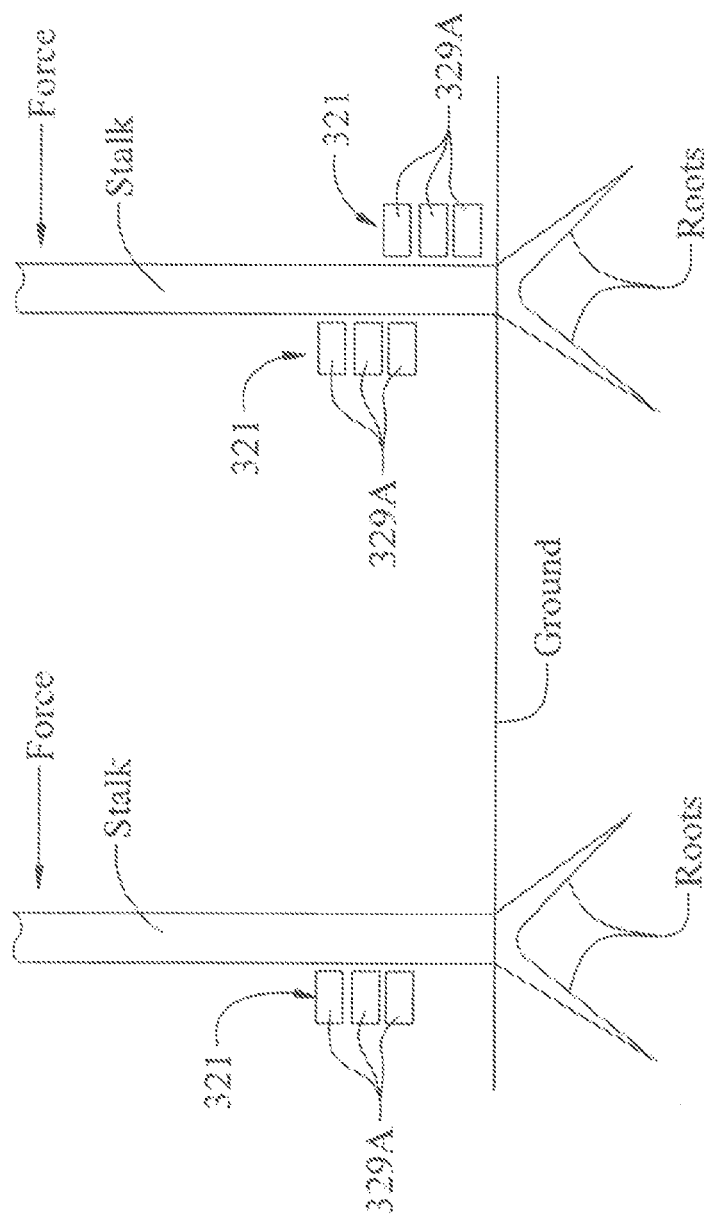
FIG. 5A is a schematic illustration of an anti-lodge assembly of the system for measuring plant stalk strength, shown in FIG. 3, in accordance with various embodiments of the present disclosure.
FIG. 5B is a schematic illustration of an anti-lodge assembly of the system for measuring plant stalk strength, shown in FIG. 3, in accordance with various other embodiments of the present disclosure.

As illustrated in FIGS. 5A and 5B, the anti-lodge bar assembly can provide support for either a single side or opposing sides of the stalks. For example, as shown in FIG. 5A, in various embodiments, the anti-lodge assembly 321 includes a first set of adjustable bars 329A that are positioned along a single side of the base of each stalk as the stalks are tested. Alternatively, in other embodiments, as shown in FIG. 5B, the anti-lodge assembly 321 can further include a second set of adjustable bars 329B. Accordingly, the first and second sets of adjustable bars 329A and 329B are positioned along opposing sides of the base of each stalk as the stalks are tested.

The system 300 further includes a data acquisition subsystem 335 for collecting, compiling and/or storing the force measurement data, e.g., torque data, transmitted from the force sensor 109 of the PSSM apparatus 100. In various implementations, the data acquisition sub-system 335 can be locally located, i.e., coupled to mounting structure 303. Or, in other implementations they can be remotely located such that the force measurement data is wirelessly transmitted to the data acquisition sub-system 335. In still other embodiments, the system 300 includes a row sensor 339 positioned between the subject row of plants and an adjacent row by a bridge structure 341 coupled to the mounting structure 303. The row sensor 339 is operable to sense a row of plants adjacent to the row of plants presently being tested. The row sensor 339 is utilized to assist in laterally positioning the PSSM apparatus 100 as the tractor 302 (shown in FIG. 3) moves along the plot of crop plants. More specifically, in various embodiments, the mounting structure 303 includes at least one extendable horizontal member 303H structured and automated, based on signals from the row sensor 339, to move the telescoping post 307, and hence the PSSM apparatus 100, laterally away from or toward the tractor 302. The extendable horizontal member (s) 303H can be structured in any manner suitable to extend, thereby moving the PSSM apparatus 100, laterally away from the tractor 302, and to retract, thereby moving the PSSM apparatus 100 laterally toward the tractor 302. For example, in various embodiments, the extendable horizontal member (s) 303H can be telescopingly structured, while in other embodiments, the extendable horizontal member(s) 303H can be structured to include a pair of slidingly engaged, e.g., tracked, components.

In such embodiments, the row sensor 339 senses, or monitors, a separation distance between the PSSM apparatus 100 and the adjacent row of plants. Then, based on the separation distance, the mounting structure 330 automatically moves the PSSM apparatus 100 laterally away from or toward the tractor 302 to maintain the proper position of the PSSM apparatus 100 with respect to the subject row of plants.

Figure 6:
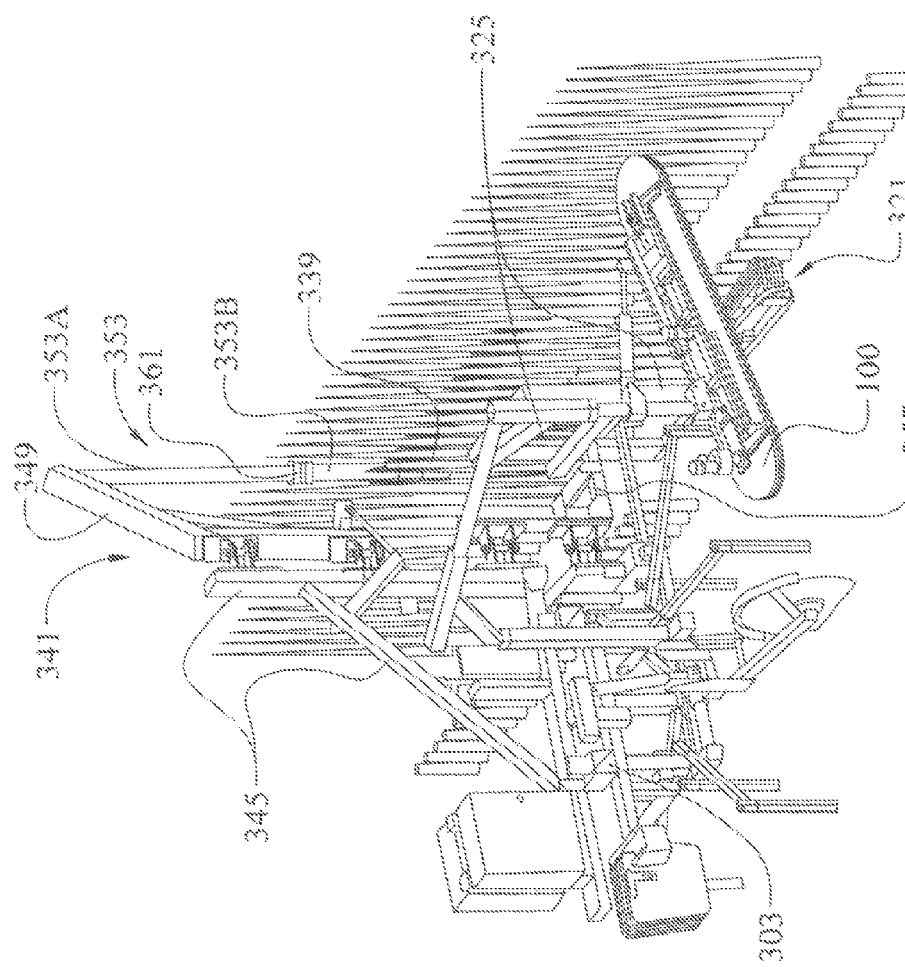
FIG. 6 is an isometric view of the system shown in FIG. 4 illustrating a row sensor swivel joint and folding hinge, in accordance with various embodiment of the present disclosure.

Referring now to FIG. 6, in various embodiments, the bridge structure 341 includes a jam structure 345 that is coupled to the mounting structure 303 and a header structure 349 hingedly connected to the jam structure 345. The bridge structure 341 additionally includes a row sensor arm 353 connected to a distal end of the header structure 349. The row sensor 339 is mounted to a distal end of the sensor arm 353. The hinged connection of the header structure 349 to the jam structure 345 allows the row sensor 339 to be generally positioned in-line with a rear axle of the tractor 302 (shown in FIG. 3). Positioning the row sensor 339 in-line with the tractor real axle limits the side-to-side movement, i.e., cross row movement of the row sensor 339 as the tractor 302 makes steering adjustments and thus, provides more accurate row tracking. Additionally, the hinged connection of the header structure 349 to the jam structure 345 allows the header 349, sensor arm 353 and row sensor 339 to be folded back to a stored position to reduce the overall size of the system 300 when the system 300 is not in use, e.g., when the system 300 is being transported via a trailer.

With further reference to FIG. 6, in various embodiments the anti-lodging assembly 321 is hingedly connected to jam structure 345 via suspension structure 357. The row sensor support arms 325 are mounted to the suspension structure 357, which is hingedly connected to the jam structure 345. The hinged connection of the anti-lodge assembly 321 to the jam structure 345 allows the anti-lodge assembly 321 to be positioned at any desired angle relative to the subject row of plant stalks. Additionally, the hinged connection of the anti-lodge assembly 321 to the jam structure 345 allows the suspension structure 357 and the anti-lodge assembly 321 to be folded back to a stored position to reduce the overall size of the system 300 when the system 300 is not in use, e.g., when the system 300 is being transported via a trailer.

Furthermore, in various embodiments, the sensor arm 353 includes a first section 353A that is connected to the distal end of the header structure 349, and a second section 353B that is rotationally connected to the first section 353A via a swivel joint 361. The swivel joint 361 allows the row sensor 339 to be positioned substantially parallel with the row of plant stalks adjacent the subject row when in use and properly stored for travel when not in use.

Figure 7:
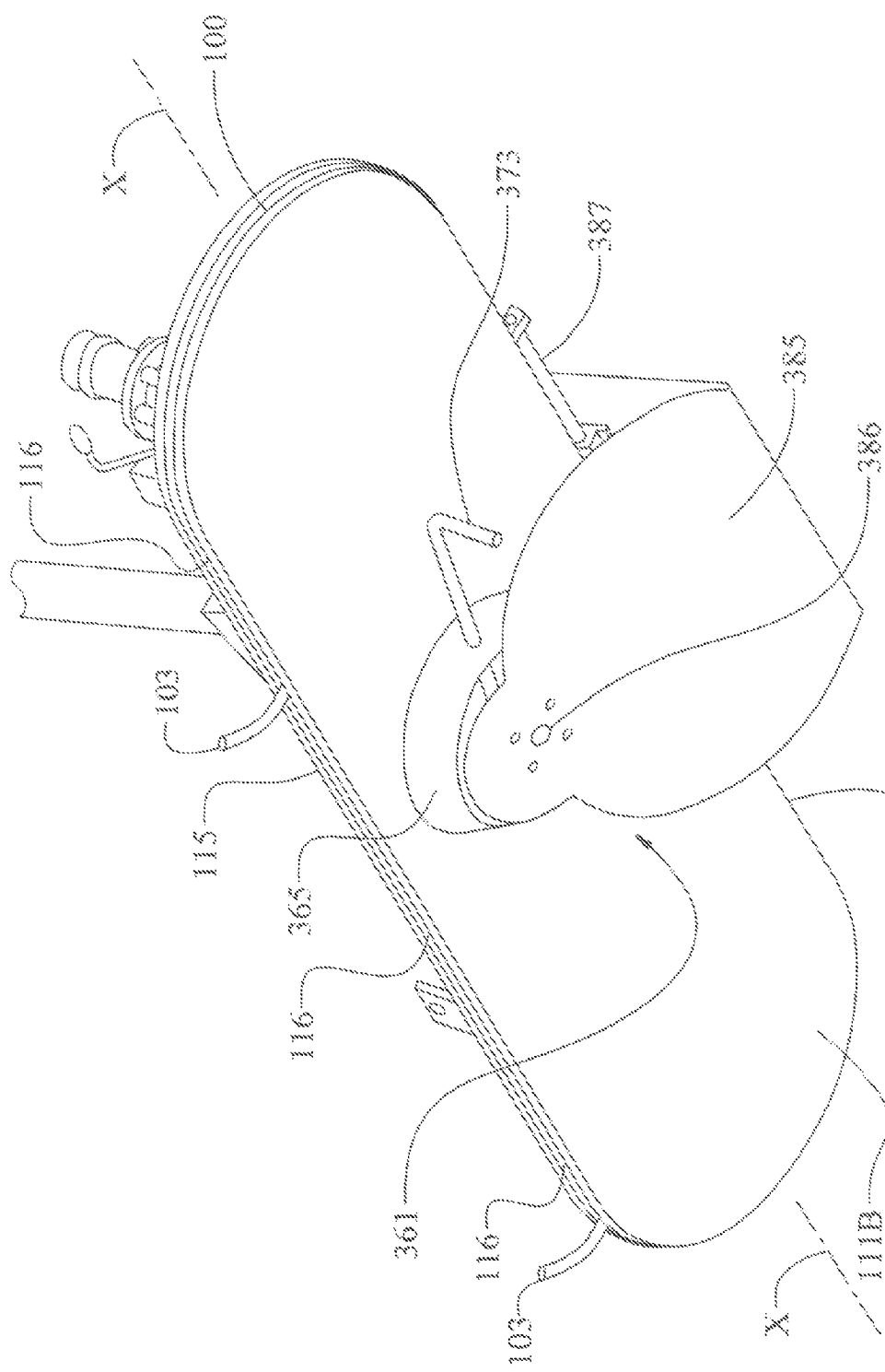
FIG. 7 is bottom isometric view of the apparatus for measuring plant stalk strength shown in FIG. 1, including a stalk sweeper assembly, in accordance with various embodiments of the present disclosure.
Figure 8:
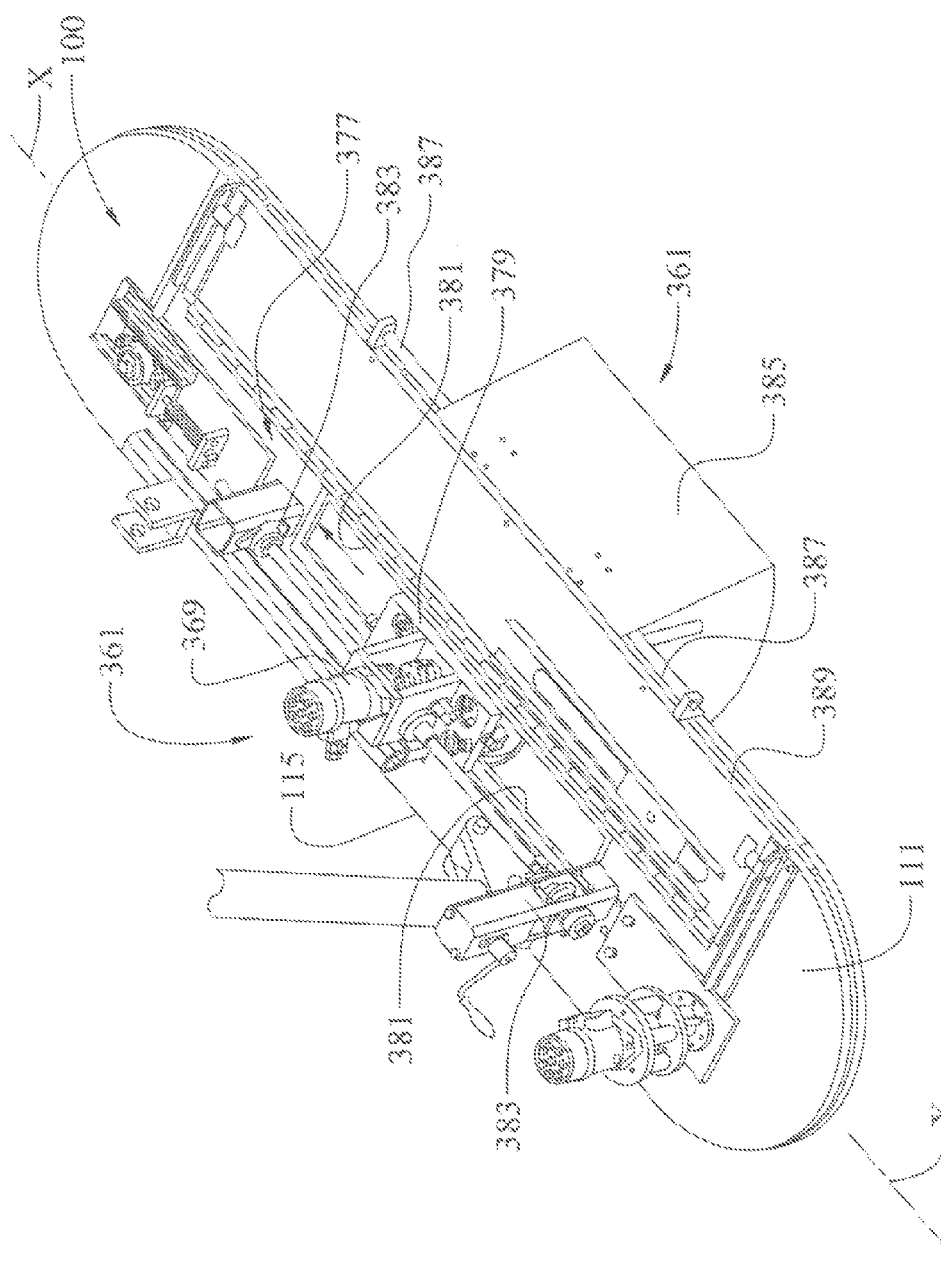
FIG. 8 is a top isometric view of the stalk sweeper assembly shown in FIG. 7, in accordance with various embodiments of the present disclosure.

Referring now to FIGS. 7 and 8, in various embodiments, the PSSM apparatus 100 includes a stalk sweeper assembly 361 that functions to remove, or clear away, previously tested stalks, i.e., broken, bent and dislodged stalks, out of the way of the next subject stalk to be tested. Clearing away the previously tested stalks ensures that only one plant stalk will be contacted and bent by each respective pulling finger 103. Therefore, both the tested stalk count accuracy and the accuracy of the force data, e.g., torque data, collected are improved. FIGS. 7 and 8 are exemplary illustrations of the PSSM apparatus 100 including the stalk sweeper assembly 361.

The stalk sweeper assembly 361 is positioned adjacent a bottom half 111B of the housing 111 and includes a hub 365 that is rotationally driven by a sweeping motor 369. The sweeping motor 369 can be any suitable rotary motor such as an electric, pneumatic or hydraulic operated rotary motor. A sweeper arm 373 is coupled to and extends radially outward from the hub 365. Thus, when the PSSM apparatus 100 is positioned and operated to test the subject row or plant stalks, as described above, the sweeping motor 369 simultaneously rotates the hub 365 and the sweeper arm 373. As the sweeper arm 373 travels in an annular path about the hub 386, the sweeper arm 373 contacts the previous tested bent, broken or dislodged plant stalks laying on the ground and moves them away from the leading edge 115 of the housing 111. Clearing the previously tested plant stalks away from the leading edge 115 provides each pulling finger 103 an unobstructed path to contact and pull the respective subsequent plant stalks.

The speed of the pulling motor 107 and the sweeping motor 369 are synchronized so that the timing, position and operation of the sweeper arm 373 is synchronized with the timing, position and operation of the conveyer and pulling fingers 103. More specifically, the operation of the sweeper motor 369 is controlled such that the sweeper arm 373 swings past the leading edge 115 between the travel of the pulling fingers 103 along the leading edge 115.

With particular reference to FIG. 8, in various embodiments, the sweeper motor 369 is mounted to a linear adjustment assembly 377 that is structured to move the sweeper motor 369 and hence, the sweeper arm 373 along a longitudinal axis X of the PSSM apparatus 100. Accordingly, the linear adjustment assembly can be operated to position the stalk sweeper assembly 361 at a desired location along the longitudinal axis X. The linear adjustment assembly 377 includes a carriage 379 to which the sweeper motor 369 is mounted. The carriage 379 is slideably mounted to carriage tracks 381. The linear adjustment assembly 377 further includes a carriage positioner assembly 383 that is operable to position and hold the carriage 379 at a desired location along the carriage tracks 381. The carriage positioner assembly 383 can be any assembly suitable to locate the carriage 379 at the desired location. For example, the carriage positioner assembly 383 can be a threaded shaft assembly, a belt and pulley assembly, a gear and chain assembly, etc.

In various embodiments, the stalk sweeper assembly 361 further includes a sweeper guard 385 coupled at a forward end to a shaft of the sweeper motor 369, or alternatively to a face of the hub 365, via a bearing 386. The sweeper guard prevents tested stalks from interfering with or getting tangled in the stalk sweeper assembly 361 and the stalk pulling components. An aft end of the sweeper guard is slidably mounted to a linear guide rail 387 mounted to a trailing edge 389 of the housing 111. Therefore, the sweeper guard 385 is structured to move along with the carriage 379 as the carriage 379 and thus, the sweeper motor 369, hub 365 and sweeper arm 373, are linearly positioned along the X axis.

In other various embodiments, the system 300 utilizes a Global Positioning System (GPS) to aid in the accurate alignment of the PSSM apparatus 100 with the subject row of plants. More specifically, the tractor 302 (shown in FIG. 3) can be automatically guided using the GPS. Thus, the GPS can be utilized to make major adjustments in the positioning of the PSSM apparatus 100 by adjusting the travel path of the tractor 302. Additionally, smaller, or micro, positioning adjustments of the PSSM apparatus 100 can be made using the automated mounting structure 303 and row sensor 339, as described above. In yet other various embodiments, the GPS can be utilized to make the major adjustments by controlling the travel path of the tractor 302 and to make the micro adjustments by controlling the operation of the automated mounting structure 303.

The methods, apparatuses and systems of the present disclosure are particularly useful in hybrid breeding programs. A key goal of hybrid breeding is to maximize yield via complementary crosses. Crosses from distinct germplasm pools that result in a yield advantage constitute heterotic groups. The identification of heterotic groups facilitates informed crosses for a yield advantage. During inbred line development, advanced inbred lines are crossed with different tester lines in order to determine how the inbred line performs in hybrid combinations. The effect of a single cross reflects the specific combining ability (SCA) and the effect of the inbred in multiple crosses with different testers (typically in multiple locations) reflects the general combining ability (GCA). Performance can be measured in terms of one or more phenotypic traits, wherein the phenotypic trait may be selected from the group comprising yield, standability, green snap susceptibility or resistance, root lodging, stalk lodging, and other agronomic traits.

In one aspect, phenotypic measurements of a trait of interest can be used as the basis for plant breeding decisions. Following characterization of stalk strength, inbreds, whether inbreds per se or inbreds in hybrid combinations, displaying strength at or above a threshold value for strength can be advanced in the breeding program, for example a corn breeding program.

In another aspect, phenotypic measurements of stalk strength can be used as the basis for breeding decisions in a corn breeding program in conjunction with genotypic data. Methods and compositions for genotyping corn plants are known in the art; for example, see US Patent Application 2006/0141495, which is incorporated herein by reference in its entirety. Phenotypic and genotypic data are evaluated for the presence of statistical associations to identify quantitative trait loci (QTL) in the corn genome contributing to stalk strength phenotypes. Methods for association studies are known in the art; non-limiting examples are provided in U.S. Pat. Nos. 5,492,547, 5,981,832, 6,219,964, 6,399,855, and 6,455,758, which are incorporated herein by reference in their entirety. Upon identification of stalk QTL, the genetic markers associated with the QTL can be used to genotype plants for the QTL alleles in order to make plant breeding decisions.

In various embodiments, the methods of the present disclosure allow one skilled in the art to make plant breeding decisions comprise the selection of progeny plants based on one or more characteristics relating to one or more stalk traits, herein termed "progeny selection." In one aspect, a population of plants will be phenotyped and only those plants with one or more preferred stalk phenotypes will be advanced to the next generation. In another aspect, a population of plants will be genotyped and only those plants with the genetic marker alleles associated with one or more stalk QTL will be advanced to the next generation.

In various other embodiments, one skilled in the art can use the methods of the present disclosure to make plant breeding decisions comprising the selection of parent plants from two or more populations for the purpose of making breeding crosses, based on one or more characteristics relating to one or more stalk traits, herein termed "parent selection." In one aspect, breeding crosses will be explicitly made based on whether one or more parent plants are previously characterized as having one or more preferred stalk phenotypes. In another aspect, breeding crosses will be explicitly made based on whether one or more parents comprise one or more marker alleles for one or more stalk QTL. The genotype data can be historic or acquired de novo.

In yet other embodiments, one skilled in the art can practice the methods of the present disclosure to make plant breeding decisions that comprise crossing a parent plant lacking one or more preferred stalk characteristics, herein termed "recurrent parent," with a parent plant comprising one or more preferred stalk characteristics followed by selection of progeny based on one or more characteristics relating to one or more stalk traits and characteristics of the recurrent parent, herein termed "trait introgression." In one aspect, a recurrent parent lacking one or more preferred stalk phenotypes is bred with a parent comprising the one or more preferred stalk phenotypes wherein selection decisions at each generation are based on preferred stalk phenotypes measurements and characteristics from the recurrent parent in order to breed a plant comprising the genetic background of the recurrent parent plus the one or more preferred stalk phenotypes. In another aspect, a recurrent parent lacking one or more stalk QTL is bred with a parent comprising the one or more stalk QTL wherein selection decisions at each generation are based on marker alleles for the stalk QTL and marker alleles from the recurrent parent in order to breed a plant comprising the genetic background of the recurrent parent plus the one or more stalk QTL.

Operation

In various exemplary configurations, the system 300 is mounted on and suspended from the back of the tractor 302 with the base of the mounting structure 303 suspended about nine inches above the ground when set up to test the strength of corn stalks. The tractor 302 (shown in FIG. 3) drives two row widths away from the subject snapping row to avoid soil compression effects by the tires. A variable speed hydraulic motor drives the drive device 105, conveyor 101 and pulling fingers 103. In some embodiments, the system 300 includes a deflecting bar 119 (shown in FIG. 2) at the top of the PSSM apparatus 100 to prevent accidental damage to plants in adjacent rows. Exemplarily, the PSSM apparatus 100 is held at an angle of from about 30° to 60°, e.g., from about 45° to 50°, from the ground to enable the fingers 103 to catch and hold the stalks. As fingers 103 travel along the leading edge 115 of the housing 111, each finger 103 hooks a respective stalk and pulls the stalk laterally and downward at the 30° to 60° until each respective stalk bends, breaks or dislodges. The force sensor 109 measures the maximum amount of resistance that each stalk produces as it is guided down the leading edge 115 of the housing 111. The data is automatically exported to data acquisition system 335 for analysis.

Most corn plants bend or break, i.e., snap, at nodes from 12" to 28" off the ground. The height of the snapping point generally correlates to the plant pickup point on the PSSM apparatus 100, i.e., the point along the lead edge 115 at which each finger 103 hooks a respective corn stalk. Best possible human steering of the tractor is generally within about 4 inches. However, as described above, the GPS and row sensor 339 can accurately maintain the PSSM apparatus 100 and thus, the pick up point, at a desired location. Maximum travel for snapping to occur is a distance of about 32.5" on the housing 111.

Although the apparatuses, systems and methods described herein are applicable to corn, the apparatuses, systems and methods are equally applicable to measuring stalk strength and root strength in other crops including wheat, canola, sunflower and sorghum.

As described above, in various embodiments, the system 300 includes the anti-lodge assembly 321 to prevent stalk lodging while measuring stalk strength because it is often not possible to test stalk strength when the ground is significantly wet. For example, in moist soil conditions, the PSSM apparatus 100 may cause the roots on one side of stalks to be pulled out of the ground.

Accordingly, for testing in moist soil conditions, the anti-lodge assembly 321 is installed and positioned to put the stalks in shear with the ground when being tested of instead of putting the roots in tension upwards, presuming that shear holding is greater than root/soil adhesion force. This would provide a pivot point, or pivot area for each stalk during testing, resulting in greatly reduced external forces at the plant base.

EXAMPLES

This example describes an experiment to determine the stalk strength and snapping resistance of corn hybrids prior to tasseling.

Two-hundred-forty hybrids, derived from twenty-three female and twenty-one male inbred lines, were tested. Line and hybrid selections were based on historical data and included to maximize the variation of green snap resistance. These hybrid selections serve as a means to check whether the machine can accurately measure distinctions across a potentially large range of hybrid susceptibilities. Tables 1 and 2 respectively show the female and male lines used in the experiment.

The test plots were planted on 2.25 acres of land at the Monsanto research farm near Huxley, Iowa. All test plots were planted in 30-inch rows. Plots for the trials were 10 feet long and 30 feet wide and had a density of 12,222 plants per acre. Nine replications were planted with a border row between each one.

The system 300 and PSSM apparatus 100 continuously snapped stalks as the tractor 302 drove down the rows. The height of the breaking point on the stalk could be adjusted by steering the tractor closer to or farther away from the plots. The system 300 used did not have a instrumentation to automatically sense and adjust the position of the PSSM apparatus 100 relative to each row. Thus, accurate driving of the tractor was critical.

On average, the system 300 was able to snap one column of 44 plots in 19.5 minutes. This time included turning the tractor 302 around, driving over the snapped stalks to flatten plants and avoid interference with machine operation during the next pass, and repositioning for another run. The design of the PSSM apparatus 100 necessitates testing in only one direction. Testing started at 6:00 AM and continued until the snapping rate decreased due to rising temperature and decreasing humidity. Hot and dry conditions later in the morning caused many of the hybrids to resist snapping beyond normal early morning levels. The hybrids tested later in the morning actually showed a trend of being more resistant to green snap when all hybrids from a replication were plotted against the mean.

Results

Tables 1 and 2 below respectively show the female and male lines used in the study. Reported Mechanical green snap general combining ability (GCA) values were calculated for each inbred as the average of green snap best linear unbiased prediction (BLUP) estimates of all hybrids containing the indicated inbred line. Historical GCA of inbred lines evaluated in the test were calculated as the average of the historical GCA of the two parental lines for the hybrid. Specific combining ability of the hybrids tested was also evaluated; however, only a small portion of the hybrids in this test had green snap data available, so this data is not presented. The GCA values were used to categorize lines into resistant, moderate, and susceptible classes. Resistant classes were those having a GCA less than 80. Moderate classes were those having a GCA between 80 and 120. Susceptible classes had a GCA over 120.

Lines were also categorized based on mechanical green snap GCA. Resistant lines were those having a mechanical GCA greater than 0.5. Moderate lines had a mechanical GCA of from about 0.5 to about –0.5. And susceptible lines had a mechanical GCA of less than –0.5.

The classifications based on the two datasets were compared for correlations.

TABLE 1

Female Lines

| Inbred | # of Hybrids | Mechanical GSP GCA | Mechanical GCA Category | Historical GCA Category |
|---|---|---|---|---|
| F1 | 1 | 1.780450 | Resistant | Resistant |
| F2 | 15 | 1.652591 | Resistant | Susceptible |
| F3 | 2 | 0.850788 | Resistant | Moderate |
| F4 | 14 | 0.579706 | Resistant | Susceptible |
| F5 | 2 | 0.471177 | Moderate | Susceptible |
| F6 | 15 | 0.364402 | Moderate | Resistant |
| F7 | 15 | 0.108332 | Moderate | Moderate |
| F8 | 15 | 0.067194 | Moderate | Moderate |
| F9 | 16 | 0.023608 | Moderate | Resistant |
| F10 | 14 | –0.036057 | Moderate | Resistant |
| F11 | 15 | –0.053418 | Moderate | Resistant |
| F12 | 14 | –0.058412 | Moderate | Moderate |
| F13 | 15 | –0.067760 | Moderate | Susceptible |
| F14 | 15 | –0.144040 | Moderate | Resistant |
| F15 | 14 | –0.248798 | Moderate | Moderate |
| F16 | 2 | –0.413078 | Moderate | Resistant |
| F17 | 16 | –0.493217 | Susceptible | Susceptible |
| F18 | 14 | –0.524905 | Susceptible | Susceptible |
| F19 | 15 | –0.532552 | Susceptible | Susceptible |
| F20 | 2 | –0.908048 | Susceptible | Resistant |
| F21 | 6 | –1.088922 | Susceptible | Moderate |
| F22 | 2 | –1.238056 | Susceptible | Moderate |
| F23 | 1 | –2.125465 | Susceptible | Resistant |

TABLE 2

Male Lines

| Inbred | # of Hybrids | Mechanical GSP GCA | Mechanical GCA Category | Historical GCA Category |
|---|---|---|---|---|
| M1 | 2 | 0.850788 | Resistant | Resistant |
| M2 | 15 | 0.809065 | Resistant | Susceptible |
| M3 | 1 | 0.472234 | Moderate | Moderate |
| M4 | 3 | 0.318098 | Moderate | Susceptible |
| M5 | 19 | 0.308415 | Moderate | Moderate |
| M6 | 15 | 0.282736 | Moderate | Resistant |
| M7 | 15 | 0.274386 | Moderate | Moderate |
| M8 | 15 | 0.260236 | Moderate | Susceptible |
| M9 | 14 | 0.220730 | Moderate | Susceptible |
| M10 | 15 | 0.139816 | Moderate | Susceptible |
| M11 | 15 | 0.116100 | Moderate | Resistant |
| M12 | 15 | 0.077392 | Moderate | Susceptible |
| M13 | 15 | 0.044058 | Moderate | Resistant |
| M14 | 15 | –0.003441 | Moderate | Resistant |
| M15 | 17 | –0.194896 | Moderate | Moderate |
| M16 | 15 | –0.396289 | Moderate | Moderate |
| M17 | 15 | –0.523944 | Susceptible | Moderate |
| M18 | 3 | –0.595321 | Susceptible | Resistant |
| M19 | 14 | –1.313334 | Susceptible | Moderate |
| M20 | 1 | –1.436315 | Susceptible | Resistant |
| M21 | 1 | –2.125465 | Susceptible | Susceptible |

The mechanical green snap GCA value is an average of BLUP estimates of all hybrids containing a given line. Mechanical GCA Category is the determination of resistance level of each line based on the mechanical green snap GCA. GCA category is GCA rankings from historic data. GCA less than 80 is classified as resistant, 80 through 120 as moderate, and greater than 120 as susceptible.

What is claimed is:

1. An apparatus for measuring at least one of stalk strength and root strength of a plant, said apparatus comprising:
   a conveyer operably connected to a motor for circulatorily driving the conveyer around at least one guide device;
   a pulling finger coupled to the conveyer and structured to contact and pull a plant stalk as the pulling finger travels around the guide device when the apparatus is positioned adjacent the plant stalk and the conveyor is driven around the guide device; and
   a force sensor for measuring resistive force encountered by the motor as the pulling finger pulls the plant stalk.

2. The apparatus of claim 1 further comprising a housing structured to cover the conveyor and cover the pulling finger during a non-pulling portion of the circulatory travel around the guide device.

3. The apparatus of claim 1 further comprising a finger sensor operable to provide finger count data used to correlate force data measured by the force sensor with respective stalks engaged by the pulling finger.

4. The apparatus of claim 1 further comprising a stalk sweeper assembly having a rotating sweeper arm for moving previously pulled stalks aside to allow the pulling finger to pull subsequent stalks absent interference from the previously pulled stalks.

5. The apparatus of claim 4, wherein the stalk sweeper comprises a sweeper guard for preventing the previous pulled stalks from interfering with the sweeper arm.

6. A system for measuring at least one of stalk strength and root strength of a crop of plants, said system comprising:
   a plant stalk strength measuring (PSSM) apparatus including:
      a conveyer operably connected to a motor for circulatorily driving the conveyer around at least one guide device,
      a plurality of pulling fingers coupled to the conveyer and structured to sequentially contact and pull each plant stalk in the crop of plants as the pulling fingers travel around the guide device when the apparatus is positioned in contact with the plant stalks and the conveyor is driven around the guide device, and
a force sensor for measuring resistive force encountered by the motor as the pulling fingers pull the plant stalks; and
a positioning mechanism mountable to a vehicle, the positioning mechanism structured to suspend and position the PSSM apparatus such that the PSSM apparatus will sequentially contact and the pulling fingers will sequentially pull each plant stalk in a subject row of the plants as the vehicle moves along the subject row of plants.

7. The system of claim 6, wherein the PSSM apparatus further comprises a finger sensor operable to provide finger count data used to correlate force data measured by the force sensor with respective stalks engaged by the pulling finger.

8. The system of claim 6, wherein the positioning mechanism comprises a mounting structure for mounting the positioning mechanism to the vehicle, and the mounting structure includes a telescoping post structured to alter a height above the ground at which the PSSM apparatus is suspended.

9. The system of claim 8, wherein the positioning mechanism further comprises a jib arm pivotally coupled to a top portion of the telescoping post and having the PSSM apparatus pivotally connected to a distal end such that the PSSM apparatus can be positioned at a desired snap angle relative to ground.

10. The system of claim 8, wherein the mounting structure further includes at least one extendable horizontal member to which the telescoping post is mounted, the at least one extendable horizontal member structured to laterally position the PSSM apparatus in a desired alignment with the subject row of plants.

11. The system of claim 6 further comprising an anti-lodge assembly attached to the mounting structure for providing support to the base of each stalk as the PSSM apparatus pulls the respective stalks.

12. The system of claim 11, wherein the anti-lodge assembly comprises one or more adjustable bars structured to be reconfigurable to provide adjustable contour shapes for bending the stalk to contact while being pulled.

13. The system of claim 6 further comprising a data acquisition sub-system for collecting force measurement data transmitted from the force sensor.

14. The system of claim 6 further comprising a global positioning system (GPS) utilized for accurately positioning the PSSM apparatus in a desired alignment with the subject row of plants.

15. The system of claim 14, wherein the vehicle utilizes the GPS to aid in steering the vehicle along a travel path adjacent the subject row of plants.

16. The system of claim 14, wherein the positioning mechanism utilizes the GPS for accurately positioning the PSSM apparatus in a desired alignment with the subject row of plants.

17. The system of claim 6 further comprising a row sensor operable to monitor a separation distance between the subject row of plants and an adjacent row of plants, wherein separation distance is utilized to assist in accurately positioning the PSSM apparatus in a desired alignment with the subject row of plants.

18. The system of claim 17 further comprising a bridge structure for suspending the row sensor between the subject row of plants and the adjacent row of plants, the bridge structure comprising at least one of:
a header hingedly connected to a jam such that the row sensor can be moved between a storage position and desired row sensing position; and
a row sensor arm having a first section and a second section rotationally connected to the first section, via a swivel joint, such that the row sensor mounted to a distal end of the second section can be angularly rotated to be placed in a desired position relative to the adjacent row of plants.

19. A method for automatically measuring at least one of stalk strength and root strength of a plurality of plants, the method comprising:
moving a plant stalk strength measuring (PSSM) apparatus along a subject row of plants;
sequentially contacting and laterally pulling plant stalks in the subject row utilizing a plurality of pulling fingers circulatorily traveling around at least one PSSM apparatus guide device; and
measuring and compiling resistive forces encountered by a motor driving the pulling fingers around the guide device as each pulling finger pulls a respective one of the plant stalks.

20. The method of claim 19, wherein moving the PSSM apparatus along the row of subject plants comprises suspending the PSSM apparatus from a positioning mechanism mounted to tractor such that the PSSM apparatus will sequentially contact and the pulling fingers will sequentially pull plant stalks in the subject row as the tractor moves along the subject row.

21. The method of claim 19, wherein measuring and compiling the resistive forces comprises correlating the force data measured for each pulled plant stalk with finger count data generated by a finger sensor of the PSSM apparatus.

22. The method of claim 19, wherein moving the PSSM apparatus along the row of subject plants comprises positioning the PSSM apparatus to have a desired snap angle relative to the ground, a desired height above the ground and a desired lateral alignment with the subject row of plants.

23. The method of claim 22, wherein positioning the PSSM apparatus comprises utilizing a global positioning system (GPS) to automatically monitor and adjust the position of the PSSM apparatus such that the desired lateral alignment of the PSSM apparatus with the subject row of plants is maintained as the PSSM is moved along the subject row of plants.

24. The method of claim 22, wherein positioning the PSSM apparatus comprises utilizing a row sensor operable to monitor a separation distance between the subject row or plants and an adjacent row of plants to automatically position the PSSM apparatus in the desired lateral alignment with the subject row of plants.

25. The system of claim 19, wherein sequentially contacting and pulling comprises positioning an anti-lodge assembly at the base of each stalk such that support is provided to the each stalk as the PSSM apparatus pulls the respective stalks.

26. The method of claim 19 further comprising making plant breeding decisions based on the compiled resistive force data.

27. The method of claim 26, wherein making plant breeding decisions comprises at least one of:
making parent selections based on the compiled resistive force data;
making progeny selections based on the compiled resistive force data and
making trait introgression selections based on the compiled resistive force data.

* * * * *